United States Patent [19]

Boatright

[11] 4,131,815

[45] Dec. 26, 1978

[54] SOLID PIEZOELECTRIC SAND DETECTION PROBES

[75] Inventor: Paul A. Boatright, College Station, Tex.

[73] Assignee: Oceanography International Corporation, College Station, Tex.

[21] Appl. No.: 771,102

[22] Filed: Feb. 23, 1977

[51] Int. Cl.² .............................................. H01L 41/10
[52] U.S. Cl. ................................. 310/323; 310/328; 310/334
[58] Field of Search ................ 340/244 R; 73/194 A, 73/194 B; 310/323, 322, 321, 328, 334

[56] References Cited

U.S. PATENT DOCUMENTS

| 2,561,763 | 7/1951 | Waters et al. | 310/328 |
| 2,746,291 | 5/1956 | Swengel | 73/194 A |
| 2,990,482 | 6/1961 | Kenny | 340/244 R |
| 3,140,859 | 7/1964 | Scarpa | 310/323 X |
| 3,771,117 | 11/1973 | Shaffer et al. | 310/336 X |
| 3,816,773 | 6/1974 | Baldwin et al. | 310/321 X |

FOREIGN PATENT DOCUMENTS 609895 12/1960 Canada .................................. 73/194 B

OTHER PUBLICATIONS

Ultrasonic Engineering by Julian R. Frederick, 1965, pp. 106, 107, 218-221.
Basic Ultrasonics by Cyrus Glickstein, 1960, p. 37.

*Primary Examiner*—Mark O. Budd
*Attorney, Agent, or Firm*—Richards, Harris & Medlock

[57] ABSTRACT

A solid probe adapted to detect the presence of sand in a fluid stream flowing through a conduit. The probe is positioned in a fluid stream and mechanically transmits the acoustical energy released when particulate matter strikes the probe to a transducer external to the probe which in turn generates an electrical signal having a frequency component representative of the particulate matter. The electrical signal is then processed to furnish information about the sand content of the flow stream.

13 Claims, 3 Drawing Figures

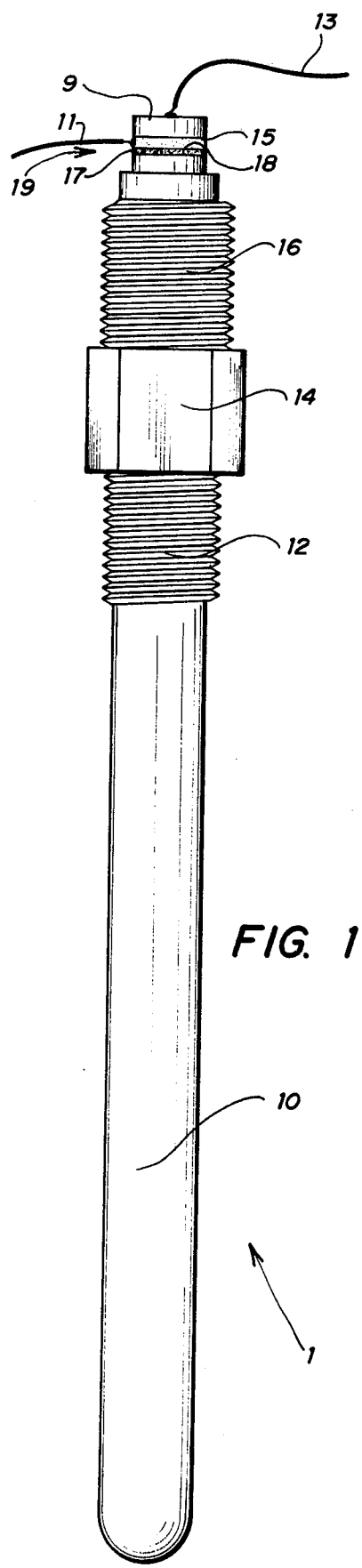
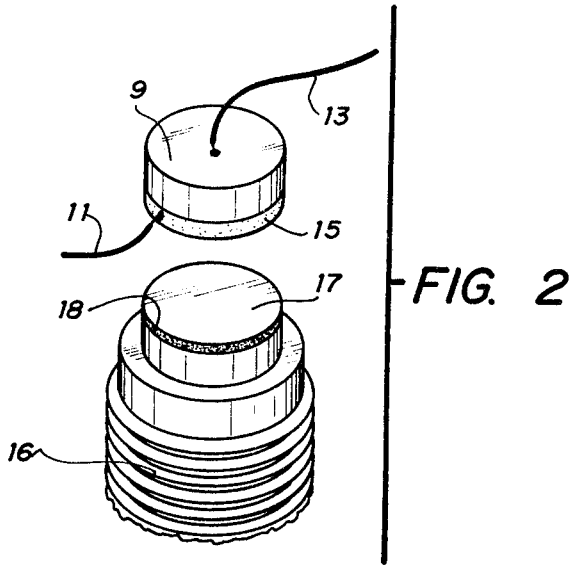
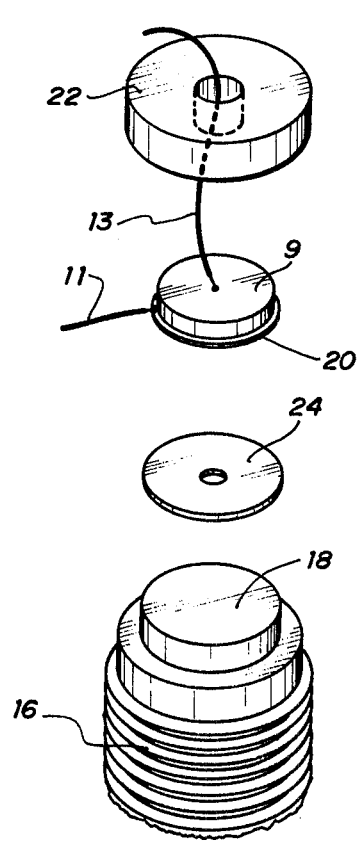

SOLID PIEZOELECTRIC SAND DETECTION PROBES

BACKGROUND OF THE INVENTION

Field of the Invention

The invention relates to a device for detecting the presence of particulate material in a fluid stream flowing through a conduit and more particularly to a probe means which is positioned directly in a production flow steam for indicating the presence of particulate material, such as sand, which is being produced along with products from an oil or gas well.

Discussion of the Prior Art

The production of fluid minerals such as oil and gas often involves accompanying particulate material, especially sand. The presence of particulate matter in fluid minerals causes the blockage of flow lines, accumulation in field separators, and damage to production equipment necessitating stoppage of production, cleaning and repair of affected equipment. It has been found that these problems can be circumvented to some extent by controlling the flow rate of produced minerals so that the volume of sand produced is maintained at an acceptable level. See U.S. Pat. No. 3,563,311, issued Feb. 16, 1971.

To maintain the flow of sand in the production of oil or gas at an acceptable level, it is necessary to monitor the production stream from a well. One type of system used to monitor the flow stream to determine wear caused by sand is the erosion probe. This type of probe is inserted directly into the flow stream where the sand will gradually erode the probe wall, at which time the pressure of the flow stream will actuate an alarm indicating that a given amount of erosion has occurred. This type of probe, however, only permits intermitent monitoring of the flow stream.

Another type of probe which permits continuous monitoring of the flow stream is coated with radioactive material. As the sand erodes away the radioactive material, the radiation reading from the probe changes, from which can be calculated the amount of sand flowing through the stream. This type of probe is disclosed in U.S. Pat. No. 3,678,273, issued July 18, 1972.

In the class of acoustical devices for detecting the presence of particulate material, there are devices which can be lowered down into the well during a cessation in production to determine if sand is present in the flow stream. Another type of device which does not require interruption of production is the acoustical flow meter disclosed in U.S. Pat. No. 3,580,092, issued to Scarpa. This acoustical device uses a piezoelectric crystal to detect the presence of particulate material in a conduit. However, this type of device detects the presence of particulate matter in the flow stream; it does not indicate with any precision the actual amount of sand flowing through the conduit.

U.S. Pat. Nos. 3,841,144 and 3,816,773, issued to Baldwin, disclose a means for detecting the presence of particulate matter such as sand in a fluid stream by using an acoustical probe positioned directly in the flow stream. The probe is a hollow cylinder, closed at one end, housing a piezoelectric crystal suspended in oil to acoustically couple the crystal to the housing. Particulate material strikes the housing of the probe which in turn excites the crystal to generate an output signal having a frequency component representative of the particulate material.

The present invention is an improvement over the Baldwin system. The solid probe used in the present invention is easier and cheaper to manufacture than the hollow housing disclosed in the Baldwin patent. Because of its solid construction, it is capable of withstanding greater pressure; it is therefore safer, cheaper to manufacture and more durable than any probe disclosed in the prior art. By locating the transducer external to the probe instead of acoustically suspending it in oil, greater signal response is achieved since the dampening of vibrations by the oil is eliminated.

SUMMARY OF THE INVENTION

The present invention may generally be described as a solid sand probe adapted to mechanically transmit acoustical vibrations imparted to the probe by the collision of particulate material in the flow stream to an acoustical transducer which, when excited, produces an electrical signal whose frequency is representative of the particulate matter. The solid sand probe comprises a solid probe, an acoustical transducer mechanically attached thereto, and a means for maintaining physical contact between the probe and the transducer which is external to the probe. The transducer may be maintained in mechanical contact with the probe by a spring-biased mechanism, by a clamp mechanism or by soldering or affixing the transducer to the backside of the probe.

DRAWINGS

A more complete understanding of the invention may be had by referring to the following detailed description when taken in conjunction with the accompanying drawings, wherein:

FIG. 1 is a side view of one embodiment of the present invention;

FIG. 2 is a partially exploded prespective of the same embodiment of the invention; and FIG. 3 is a partially exploded perspective of another embodiment of the invention.

DETAILED DESCRIPTION

Referring more particularly to the drawings, FIG. 1 discloses a solid sand probe 1 with an acoustical transducer 19 soldered to the backside 18 of the probe 1. The probe is essentially a solid cylinder 10 with threaded pipe fittings at one end and a rounded portion at the opposite end which is inserted into the conduit. An exemplary material for construction of the probe is stainless steel because of its low cost and durability. Any durable material, however, which can effectively transmit acoustical energy can be used. For example the probe could also be made of ceramic material. The extension of the probe proper 10 must be sufficient to provide a collision barrier to substantially all particulate matter in the flow stream. The length of the probe proper, therefore, will vary with the width of the conduit. In positioning the probe proper 10 in the conduit, care must be taken to assure that the probe extends well below the central axis of the conduit, because the greatest concentration of sand in a flow stream will occur in the lower portion of the conduit due to the action of natural gravitational forces. To counteract the erosive effect of the particulate matter on the probe in the conduit, the probe proper 10 may be coated with a thin layer of wear-resistant material such as titanium carbide to extend its operational life.

Extending from the opposite end of the probe proper 10 are the threaded portions 16 and 12. Threaded portion 12 adjacent the probe proper 10 is designed to permit the probe to be screwed into a pipe fitting in the conduit (not shown) perpendicular to the flow stream. Adjacent the threaded portion 12 of the probe 1 is a hexagonal pipe fitting 14 adapted to receive a wrench to screw probe proper 10 into the conduit. Adjacent to the hexagonal fitting 14 is threaded portion 16 which may be used to anchor a bolting or clamping device for the purpose of maintaining the acoustical transducer 19 in constant mechanical contact with the probe. Adjacent the threaded portion 16, the probe tapers in steps so that the backside 18 is roughly the same circumference as the attached transducer 19. The backside 18 of the probe is flat, adapted to make contact with a flat surface of the acoustical transducer 19.

Acoustical transducer 19 consists of a piezoelectric crystal 9 having output lead 13 connected to an external electrical system for processing the output signal and a ground lead 11. The piezoelectric crystal has its output signal externally tuned to the primary resonant frequency of its thickness mode. This provides a peaked output signal at the tuned frequency while most other frequencies in the output signal are attenuated. For detection of particulate material, the primary resonant frequency must be above 100 kHz for reasons indicated hereafter. The transducer 19 is tuned externally and the signal electrically generated by the influx of acoustical energy is processed by external electrical circuitry and converted to usable information.

The piezoelectric crystal 9 is a ceramic crystal in the shape of a circular disk or wafer. A peizoelectric crystal should be selected which has a primary resonant frequency in one of its thickness modes of approximately 700 kHz, well above the minimum 100 kHz frequency range required for positive detection of particulate material in the flow stream. It is necessary to have a response frequency in the thickness mode well above 100 kHz, because such crystals usually resonate in the radial mode at approximately 100 khz and because pump and other extraneous noises may contain frequency components in the 100 kHz range. Reliance upon a 700 kHz range signal permits detection of a "clean" signal representative of the acoustical energy imparted by a collision of particulate material with the probe proper 10. The external electrical circuitry amplifies and filters the output signal so that the mass of the sand in a flow stream can be calculated. This can be accomplished by independently measuring the flow and obtaining the mass by table lookup or by the method and apparatus disclosed in the application copending herewith.

A variety of means are available for acoustically linking the probe with the transducer. It is critical that whatever method is chosen, the acoustical couple be sufficiently shock resistant and of sufficient strength to maintain the transducer against the backside of the probe with sufficient force to insure effective mechanical transmission of acoustical energy at the junction therebetween.

FIGS. 1 and 2 show one embodiment of the invention wherein the acoustical transducer 19 is soldered to a stainless steel probe proper 10. A layer of silver solder 17 is applied to the backside 18 of the probe 1 because ordinary solder cannot be used on stainless steel. A coat of low melting point solder 15 is then applied to the crystal face which is bonded to the coating of silver solder to create a joint which gives optimum coupling and improved shock resistance.

FIG. 3 shows another embodiment of the invention wherein the crystal 9 is mechanically clamped to the backside 18 of the probe 1. The crystal 9 is electrically insulated from the backside of the probe 1 by interposition of a mica washer 24 between the crystal 9 and the probe 1. The crystal 9 is mounted on a thin brass plate 20 to which is attached ground lead 11. Adjacent the top surface of crystal 9 is reaction mass 22 containing an aperture designed to permit the output lead 13 from crystal 9 to pass therethrough. Reaction mass 22 is clamped or bolted to the probe 1 by means of a clamp mechanism which is anchored in the rear portion of the probe. Threads 16 may be used to screw the probe 1 into the clamp mechanism (not shown).

The transducer 19 may also be maintained in constant mechanical contact with the backside 18 of probe 1 by means of a spring-biased mechanism, anchored on probe 1 by means of a fitting designed to receive the threaded portion 16 of the probe 1.

An alternative method of mounting the transducer is to use a strong adhesive such as epoxy.

When the sand in the flow stream of the conduit collides with the probe proper 10, a portion of the kinetic energy of the particle is translated into acoustical energy which is then transmitted through the probe proper 10 to the piezoelectric crystal 9 in mechanical contact therewith. The force applied to the crystal causes a deformation in the crystal, which creates a charge on the crystal surface, resulting in an output signal having a frequency in the 700 kHz range, indicative of a collision between a sand particle and the probe. The electrical output signal is then transmitted to an external electrical system tuned to the primary resonant frequency of the crystal which amplifies the signal, filters it and converts it into useful information from which the mass or mass flow from a given time can be determined.

Although particular embodiments of the invention have been illustrated in the drawings and described herein, it will be understood that the invention is not limited to the embodiments disclosed, but is capable of rearrangement, modification and substitution of parts and elements without departing from the spirit of the invention.

What is claimed is:

1. An apparatus for detecting the presence of particulate matter in a fluid stream flowing through a conduit, said aparatus comprising:

an acoustical probe means for detecting the presence of particulate matter in a moving fluid stream, said probe means responsive to the presence of particulate matter in the fluid stream and relatively unresponsive to the movement of said fluid, said probe means having, a solid probe adapted to be inserted into a conduit and to be in contact with said fluid stream;

an acoustical transducer disposed adjacent said probe in mechanical contact therewith, responsive to acoustical energy imparted by the collision of particulate matter with said probe, said transducer generating an electrical signal corresponding to the influx of acoustical energy from the collision of the particulate matter with said probe; and means for maintaining said transducer in constant mechanical contact with said probe for transmitting acoustical energy from said probe to said transducer.

2. The apparatus defined in claim 1 wherein a thin layer of wear-resistant material is applied to the outer surface of said probe to retard erosion by particulate matter in the fluid stream.

3. The apparatus defined in claim 1 wherein said probe is manufactured of a metallic substance.

4. The apparatus defined in claim 1 wherein said acoustical transducer comprises:
   a piezoelectric crystal responsive to frequencies generated by particulate matter colliding with said probe; and
   an output lead transmitting the electrical response of said crystal to an external electrical system for processing.

5. The apparatus defined in claim 4 wherein said piezoelectric crystal is shaped as a circular disk and has a primary resonant frequency in its thickness mode in excess of 100 kHz.

6. The apparatus defined in claim 5 wherein the primary resonant frequency of the piezoelectric crystal in its thickness mode is about 700 kHz.

7. The apparatus defined in claim 1 wherein said means for maintaining said transducer in mechanical contact with said probe is a spring-biased mechanism which retains said probe and said transducer in constant mechanical contact at sufficient pressure to effectively transmit acoustical energy therebetween.

8. The apparatus defined in claim 1 wherein said means for maintaining said transducer in mechanical contact with said probe is a layer of adhesive interposed therebetween which retains said probe and said transducer in constant mechanical contact to effectively transmit acoustical energy.

9. The apparatus defined in claim 1 wherein said means for maintaining said transducer in physical contact with said probe comprises:
   an electrically insulated washer placed between said probe and said crystal;
   a reaction mass placed between said crystal and said clamping means; and
   a clamping means anchored on said probe and attached to said reaction mass maintaining said crystal in constant mechanical contact with said probe.

10. The apparatus defined in claim 1 wherein said means for maintaining said transducer in constant mechanical contact with said probe comprises:
   a layer of low melting point solder applied to said crystal interface; and
   a layer of silver solder applied to the backside of said probe in electrical and mechanical contact with said low melting point solder to maintain said probe and said crystal in constant mechanical contact with said probe to effectively transmit acoustical energy therebetween.

11. An apparatus for detecting the presence of particulate matter in a fluid stream flowing through a conduit, said apparatus comprising:
   an acoustical probe means for detecting the presence of particulate matter in a moving fluid stream, said probe means responsive to the presence of particulate matter in the fluid stream and relatively unresponsive to the movement of the fluid, said probe means having,
   a solid metallic probe adapted to be inserted into a conduit so as to be in mechanical contact with said fluid stream;
   a piezoelectric crystal disposed adjacent said probe in mechanical contact therewith, said crystal being responsive to frequencies generated by particulate material colliding with said probe and said crystal shaped as a circular disk having a primary resonant frequency in its thickness mode of about 700 kHz;
   an output lead transmitting the electrical response of said crystal to an external electrical system for processing; and
   a clamp means for maintaining said crystal in constant mechanical contact with said probe, said means comprising an electrically insulated washer interposed between said probe and said crystal, a reaction mass adjacent said crystal, and one of a clamp or bolt attaching said probe to said mass.

12. An apparatus for detecting the presence of particulate matter in a fluid stream flowing through a conduit, said apparatus comprising:
   an acoustical probe means for detecting the presence of particulate matter in a moving fluid stream, said probe means responsive to the presence of particulate matter in the fluid stream and relatively unresponsive to the movement of the fluid, said probe means having,
   a solid metallic probe adapted to be inserted into a conduit so as to be in constant mechanical contact with said fluid stream;
   a piezoelectric crystal disposed adjacent said probe in mechanical contact therewith, said crystal being responsive to frequencies generated by particulate matter colliding with said probe, said crystal shaped as a circular disk having a primary resonant frequency in a thickness mode of about 700 kHz;
   an output lead transmitting the electrical response of said crystal to an external electrical system for processing; and
   means for maintaining said crystal in constant mechanical contact with said probe, said means comprising a layer of silver solder applied to the backside of said probe, and a layer of low melting point solder interposed between said layer of silver solder and said piezoelectric crystal.

13. A apparatus for detecting the presence of particulate matter in a fluid stream flowing through a conduit, said apparatus comprising:
   an acoustical probe means for detecting the presence of particulate matter in a moving fluid stream, said probe means responsive to the presence of particulate matter in the fluid stream and relatively unresponsive to the movement of the fluid, said probe means having,
   a solid metallic probe adapted to be inserted into a conduit so as to be in constant mechanical contact with said fluid stream;
   a piezoelectric crystal disposed adjacent said probe in mechanical contact therewith, said crystal being responsive to frequencies generated by particulate matter colliding with said probe, said crystal shaped as a circular disk having a primary resonant frequency in a thickness mode of about 700 kHz;
   an output lead transmitting the electrical response of said crystal to an external electrical system for processing; and
   means for maintaining said crystal in constant mechanical contact with said probe, said means comprising a layer of epoxy interposed between said probe and said crystal.

* * * * *

Disclaimer 4,131,815.—*Paul A. Boatright,* College Station, Tex. SOLID PIEZOELECTRIC SAND DETECTION PROBES. Patent dated Dec. 26, 1978. Disclaimer filed Mar. 28, 1983, by the assignee, *Oceanography International Corp.*

Hereby enters this disclaimer to all claims of said patent.

[*Official Gazette June 7, 1983.*]